(12) United States Patent
Chen et al.

(10) Patent No.: US 10,196,395 B2
(45) Date of Patent: Feb. 5, 2019

(54) CRYSTALLINE FORM ALPHA OF IPI-145 AND PREPARATION METHOD THEREOF

(71) Applicant: CRYSTAL PHARMATECH CO., LTD., Suzhou, Jiangsu (CN)

(72) Inventors: Minhua Chen, Jiangsu (CN); Yanfeng Zhang, Suzhou (CN); Xiaojuan Diao, Suzhou (CN); Nan Xia, Suzhou (CN); Xiaoyu Zhang, Suzhou (CN)

(73) Assignee: Crystal Pharmatech Co., Ltd, Suzhou (CN)

( * ) Notice: Subject to any disclaimer, the term of this patent is extended or adjusted under 35 U.S.C. 154(b) by 0 days.

(21) Appl. No.: 15/562,988

(22) PCT Filed: Feb. 1, 2016

(86) PCT No.: PCT/CN2016/073071
§ 371 (c)(1),
(2) Date: Sep. 29, 2017

(87) PCT Pub. No.: WO2016/127844
PCT Pub. Date: Aug. 18, 2016

(65) Prior Publication Data
US 2018/0072733 A1   Mar. 15, 2018

(30) Foreign Application Priority Data
Feb. 12, 2015 (CN) .......................... 2015 1 0075964

(51) Int. Cl.
| | | |
|---|---|---|
| *C07D 473/34* | (2006.01) | |
| *C07D 473/30* | (2006.01) | |
| *A61K 31/52* | (2006.01) | |

(52) U.S. Cl.
CPC ............. *C07D 473/34* (2013.01); *A61K 31/52* (2013.01); *C07D 473/30* (2013.01); *C07B 2200/13* (2013.01)

(58) Field of Classification Search
CPC ............. C07D 473/34; C07D 473/30; C07B 2200/13; A61K 31/52
See application file for complete search history.

(56) References Cited

U.S. PATENT DOCUMENTS

2012/0184568 A1* 7/2012 Ren .................. C07D 473/34
514/263.22

FOREIGN PATENT DOCUMENTS

| WO | WO-2012160568 A1 * | 11/2012 | ........... A61K 31/337 |
|---|---|---|---|
| WO | 2015014315 A1 | 2/2015 | |

OTHER PUBLICATIONS

Cains, P.W., Polymorphism in Pharmaceutical Solids 2009 Ed. H.G. Brittain, Informa Healthcare Chapter 4: 76-138.*
Mino R. Caira, Crystalline Polymorphism of Organic Compounds, Topics in Current Chemistry, vol. 198, pp. 163-208, 1998.

* cited by examiner

*Primary Examiner* — John M Mauro
(74) *Attorney, Agent, or Firm* — VLP Law Group LLP; Kent H. Cheng

(57) ABSTRACT

The present disclosure relates to crystalline Form α of a compound of formula (I) used for preparing a blood-cancer drug and preparation method thereof. The crystalline Form α in the present disclosure has better stability, and its solubility and hygroscopicity meet the requirements of medical use. Form α has simple preparation method and low manufacturing cost, and provides great value to future optimization and development of this drug.

(I)

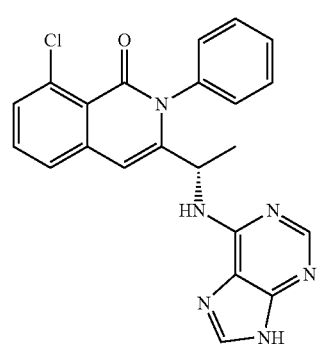

11 Claims, 4 Drawing Sheets

CRYSTALLINE FORM ALPHA OF IPI-145 AND PREPARATION METHOD THEREOF

TECHNICAL FIELD

The present disclosure relates to the field of pharmaceutical chemistry, particularly relates to crystalline Form α of IPI-145, for treatment of blood cancer, and preparation method thereof.

BACKGROUND

Infinity Pharmaceutical's Duvelisib (previously known as: IPI-145, INK1197) for treatment of blood cancer is a novel oral phosphoinositide 3-kinase (PI3K) δ/γ dual-target inhibitors. Currently, Duvelisib (IPI-145) is in clinical studies for the treatment of chronic lymphocytic leukemia (CLL) and inert non-Hodgkin's lymphoma (iNHL). Infinity pharmaceutical got the worldwide exclusive rights of Duvelisib (IPI-145) from Takeda's subsidiary Intellikine in 2011. The chemical name of Duvelisib is: (S)-3-(1-(9H-purin-6-ylamino) ethyl)-8-chloro-2-phenylisoquinolin-1(2H)-one and the structure is shown as Formula (I):

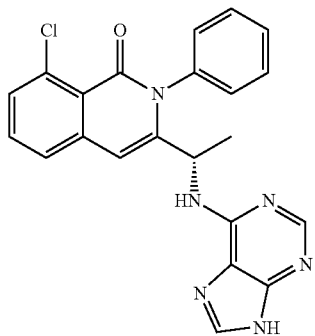

For solid chemical drugs, different crystalline forms have different solubility and stability, which will affect the absorption and bioavailability of the drug, finally leading to the differences in clinical efficacy. Therefore, it is necessary to perform polymorph screening comprehensively and systematically and to get the crystalline form that is most suitable for development.

CN103648499A discloses several crystalline forms of formula (I), including Form A, Form B, Form C, Form D, Form E, Form F, Form G, Form H, Form I and Form J. Among those crystalline forms: Form B is prepared by heating Form A at a high temperature; After grinding, the crystallinity of Form C, Form D, Form E decrease or turns into amorphous; Form F, Form G, Form H, Form I are solvates; Only Form A is a relatively stable anhydrate and suitable for development.

SUMMARY

The crystalline Form α of compound of formula (I) provided in the present disclosure has good stability, and the solubility and hygroscopicity meet the requirements of medical use, and the preparation method is simple, and has low cost, which is of great value for the future optimization and development of the drug.

A crystalline Form α of compound of formula (I), the structure of the compound of formula (I) is:

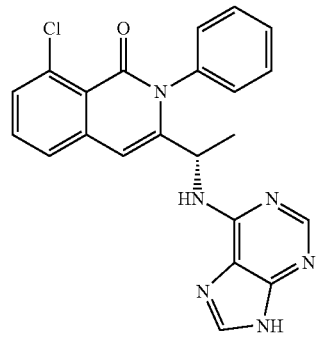

The X-ray powder diffraction pattern of Form α has characteristic peaks at 2theta values of 11.1°±0.2°, 22.3°±0.2°, 18.1°±0.2°.

Further, the X-ray powder diffraction pattern of Form α has characteristic peaks at 2theta values of 15.5°±0.2°, 17.2°±0.2°, 28.8°±0.2°, 5.5°±0.2°.

Further, the X-ray powder diffraction pattern of the Form α is substantially as shown in FIG. 1.

Form α of the present disclosure, an endothermic peak appears when heated to around 214° C., a sharp exothermic peak appears when heated to around 256° C., and the second endothermic peak appears when heated to around 282° C. The differential scanning calorimetry analysis thermogram is substantially as shown in FIG. 2.

Form α of the present disclosure, a weight loss of about 2.5% when heated to around 250° C. The thermal gravimetric analysis thermogram is substantially as shown in FIG. 3.

The present disclosure provides a process for preparing Form α of Formula (I). The compound of Formula (I) is added into crystallization solvents to obtain a suspension, the suspension is stirred at 40° C.-60° C. and filtered to obtain clear solution. Then the clear solution is cooled to −20° C.-−10° C. to obtain a solid, and the solid is crystalline Form α.

Preferably, the solid of the compound of Formula (I) is added into crystallization solvents to obtain a suspension; the suspension is stirred at 45° C.-55° C. and filtered to obtain clear solution. Then the clear solution is cooled to 2° C.-8° C. to obtain solid, and the solid is crystalline Form α.

Further, said crystallization solvents selected from the one or more solvents comprising: alcohols, ketones, esters, aromatic hydrocarbons, halogenated hydrocarbons, nitriles, nitroparaffins, cyclic ethers and fatty hydrocarbons.

More further, said crystallization solvent is tetrahydrofuran.

The present invention further provides another process for preparing crystalline Form α of Formula (I). The compound of Formula (I) is dissolved into crystallization solvents to obtain clear solution, than clear solution is evaporated at 10° C.-30° C. until solid precipitated. The solid is the crystalline Form α.

Further, said crystallization solvent selected from the one or more solvent comprising: alcohols, ketones, esters, aromatic hydrocarbons, halogenated hydrocarbons, nitriles, nitroparaffins, cyclic ethers and fatty hydrocarbons.

More further, said crystallization solvent is tetrahydrofuran.

A pharmaceutical composition, said pharmaceutical composition comprises Form α and pharmaceutically acceptable excipients.

The present disclosure also provides use of Form α in the preparation of anti-cancer drugs.

The present disclosure also provides use of Form α in the preparation of drugs for the treatment of chronic lymphocytic leukemia and inert non-Hodgkin's lymphoma.

The advantages of the present disclosure are as follows:

Form α provided by the present disclosure is more thermodynamic stable than Form A in CN103648499A, thus Form α can avoid crystal transformation during drug development and storage, thereby avoid the change of drug solubility, dissolution rate, bioavailability and efficacy.

The crystalline form provided by the present disclosure has low hygroscopicity and meets the requirements of bioavailability and efficacy. The manufacturing process does not need special drying conditions, thus simplifies the preparation and the post-treatment process. The crystalline form provided by the present disclosure does not easily affected by humidity, thus it is not strict with storage conditions and suitable for long term storage, which greatly reduce the cost of storage and quality control, thus have strong economic value.

DETAILED DESCRIPTION

The present disclosure will be further explained by the specific embodiments, but are not intended to limit the scope of the present disclosure. The skilled in the art can make improvements to the process of preparation and the used instruments within the scope of the claims, and those improvements should be considered as falling into the scope of the present disclosure. Therefore, the protective scope of the present disclosure patent should be defined by the claims.

In the following examples, the test methods are generally carried out in accordance with conventional conditions or conditions recommended by the manufacturer.

The abbreviations used in the present disclosure are explained as follows:

XRPD: X-ray Powder Diffraction
DSC: Differential Scanning calorimetry
TGA: Thermal Gravimetric Analysis
DVS: Dynamic Vapor Sorption
RH: Relative Humidity X-ray powder diffraction pattern in the present disclosure was acquired by Panalytical Empyrean X-ray powder diffraction. The parameters of the X-ray powder diffraction method of the present disclosure were as follows:

X-ray reflection parameters: Cu, Kα
Kα1 (Å): 1.540598; Kα2 (Å): 1.544426
Kα2/Kα1 intensity ratio: 0.50
Voltage: 45 (kV)
Current: 40 (mA)
Scan range: from 3.0° to 40.0°

Differential scanning calorimetry (DSC) thermogram in the present disclosure was acquired by a TAQ2000. The parameters of the differential scanning calorimetry method of the present disclosure were as follow:

The scan rate: 10° C./min
Purge gas: nitrogen

Thermal gravimetric analysis (TGA) thermogram in the present disclosure was acquired by a TAQ5000. The parameters of the thermal gravimetric analysis (TGA) method of the present disclosure were as follow:

The scan rate: 10° C./min
Purge gas: nitrogen

Dynamic Vapor Sorption (DVS) was measured via Dynamic Vapor Sorption Intrinsic manufacture by SMS's (Surface Measurement Systems Ltd.). Typical Parameters for DVS test were listed below.

Temperature: 25° C.
Gas and flow rate: $N_2$, 200 mL/min
dm/dt: 0.002%/min
RH range: 0% RH to 95% RH Example 1

Process for Preparing Crystalline Form α of Compound of Formula (I):

10.9 mg of compound of Formula (I) was added into 0.5 mL tetrahydrofuran to obtain a suspension, the suspension was stirred in incubator at 50° C. for 100 minutes, than filtered to obtain a clear solution. The clear solution was cooled to 5° C. at a rate of 100° C./min and solid precipitation was obtained. The solid precipitation solution was centrifuged and dried at 25° C. in incubator overnight, and the obtained solid is crystalline Form α.

Figure 1:
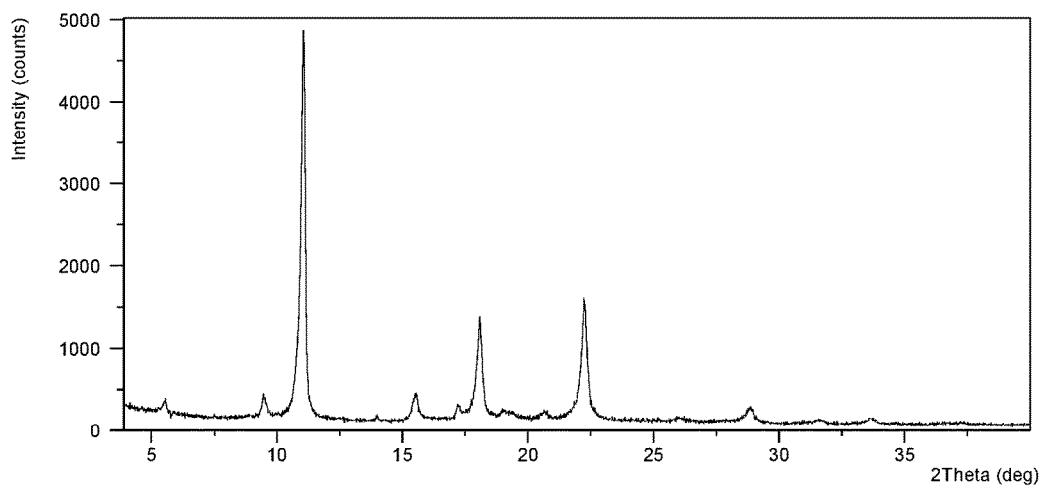
FIG. 1 shows the XRPD pattern of Form α.
Figure 2:
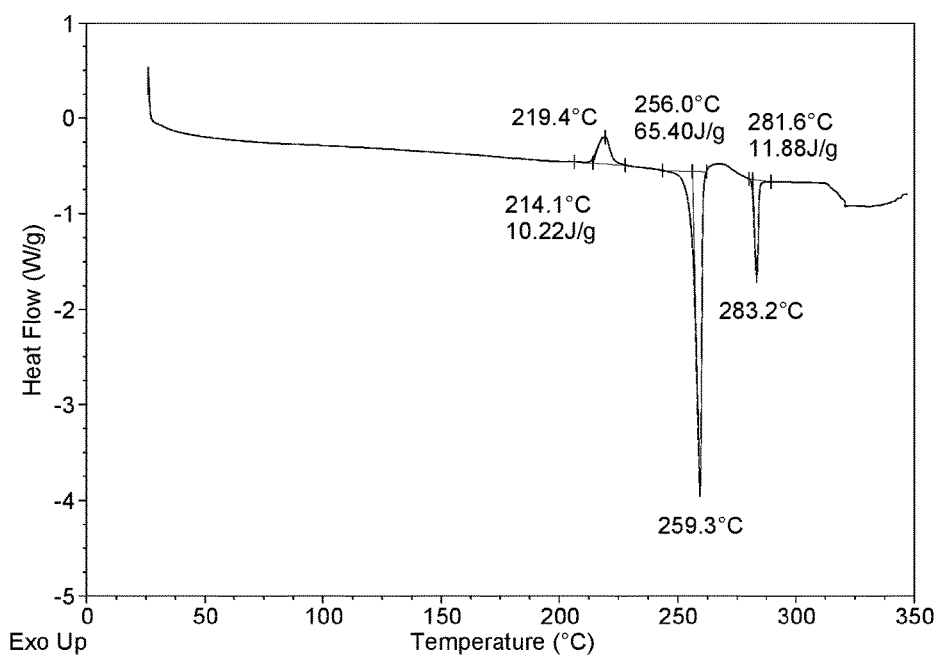
FIG. 2 shows the DSC thermogram of Form α.
Figure 3:
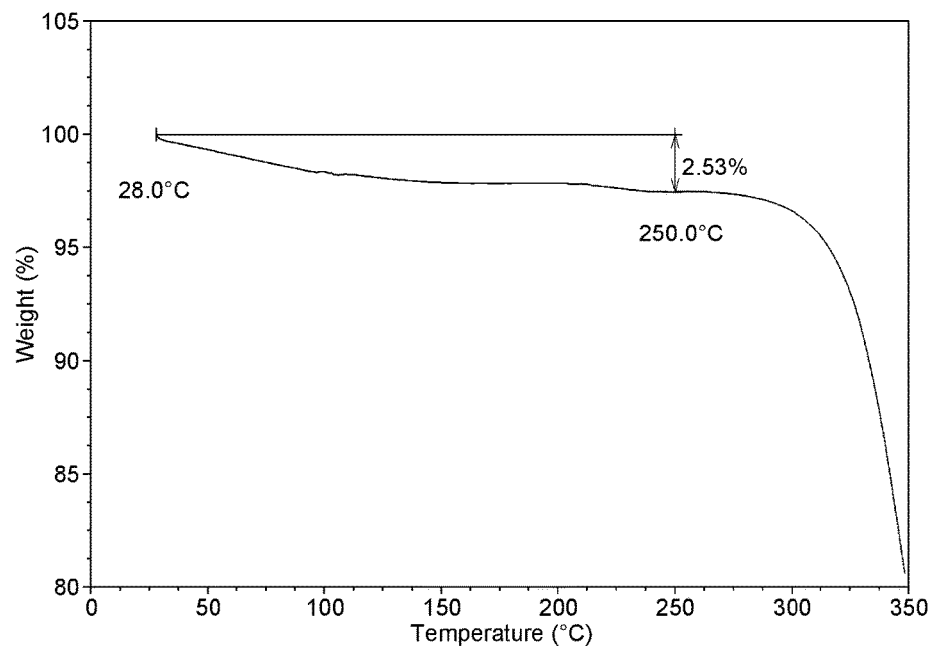
FIG. 3 shows the TGA thermogram of Form α.

The X-ray powder diffraction data of crystalline form of the present example is displayed in Table 1, the XRPD pattern is displayed in FIG. 1, DSC thermogram is displayed in FIG. 2, and TGA thermogram is displayed in FIG. 3.

Figure 4:
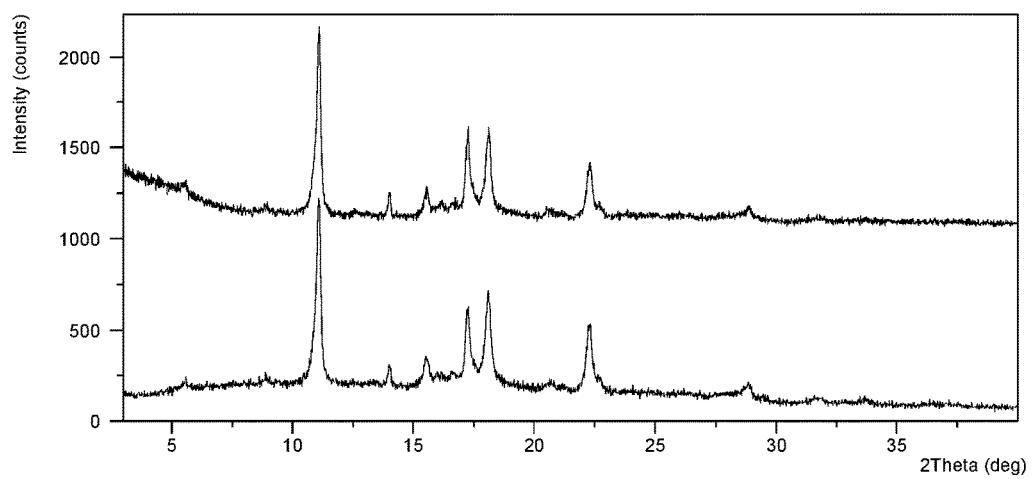
FIG. 4 shows the XRPD pattern of Form α prepared by example 1 before and after placing at 5° C. for 300 days (the above pattern shows the XRPD before placing, the below pattern shows the XRPD after placing for 300 days)

The X-ray powder diffraction of the crystalline form in the present example is tested after placed at 5° C. condition for 300 days, the XRPD pattern is displayed in FIG. 4.

Figure 5:
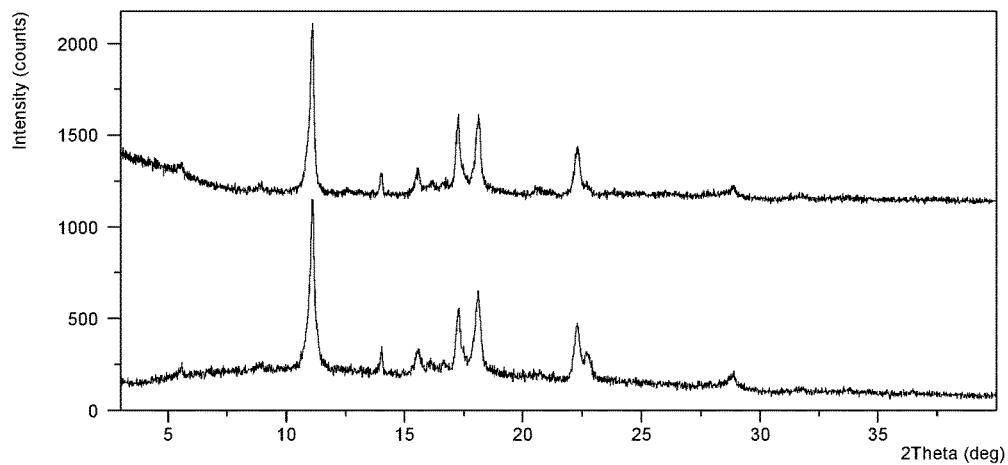
FIG. 5 shows the XRPD patterns of Form α prepared by example 1 before and after placing at 25° C., 60% RH for 300 days (the above pattern shows the XRPD before placing, the below pattern shows the XRPD after placing for 300 days)

The X-ray powder diffraction of the crystalline form in the present example is tested after placed at 25° C. and 60% RH for 300 days, the XRPD pattern is displayed in FIG. 5.

Figure 6:
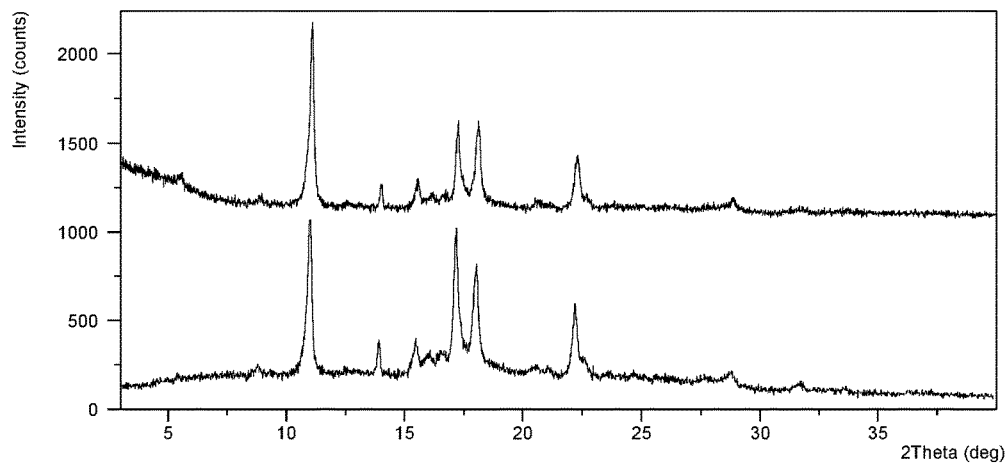
FIG. 6 shows the XRPD patterns of Form α by example 1 before and after placing at 40° C., 75% RH for 300 days (the above pattern shows the XRPD before placing, the below pattern shows the XRPD after placing for 300 days)

The X-ray powder diffraction of the crystalline form in the present example is tested after placed at 25° C. and 60% RH for 300 days, the XRPD pattern is displayed in FIG. 6.

TABLE 1

| 2theta | d spacing | intensity % |
|---|---|---|
| 5.51 | 16.03 | 2.94 |
| 9.48 | 9.33 | 5.78 |
| 11.06 | 8.00 | 100.00 |
| 13.96 | 6.34 | 1.35 |
| 15.51 | 5.71 | 6.80 |
| 17.21 | 5.15 | 3.89 |
| 18.05 | 4.91 | 26.68 |
| 19.10 | 4.65 | 2.16 |
| 20.65 | 4.30 | 2.21 |
| 22.25 | 4.00 | 30.35 |
| 26.02 | 3.42 | 0.85 |
| 28.82 | 3.10 | 3.69 |

TABLE 1-continued

| 2theta | d spacing | intensity % |
| --- | --- | --- |
| 31.55 | 2.84 | 0.87 |
| 33.66 | 2.66 | 1.43 |

Example 2

Process for Preparing Crystalline Form α of Compound of Formula (I):

101.7 mg of compound of Formula (I) was added into 6.0 mL tetrahydrofuran to obtain a suspension, the suspension was stirred in incubator at 50° C. for 100 minutes and filtered to obtain a clear solution, then the clear solution was cooled to 5° C. at a rate of 0.1° C./min and solid precipitation was obtained. The solid precipitation solution was centrifuged and then dried at 25° C. in incubator overnight, and the obtained solid is crystalline Form α.

The XRPD data of the solid prepared in present example is displayed in Table 2.

TABLE 2

| 2theta | d spacing | intensity % |
| --- | --- | --- |
| 5.46 | 16.18 | 10.79 |
| 11.06 | 8.00 | 100.00 |
| 13.94 | 6.35 | 7.39 |
| 15.49 | 5.72 | 11.13 |
| 17.19 | 5.16 | 21.23 |
| 18.05 | 4.91 | 37.71 |
| 20.62 | 4.31 | 2.10 |
| 22.25 | 4.00 | 31.50 |
| 25.95 | 3.43 | 1.51 |
| 28.80 | 3.10 | 5.15 |
| 31.61 | 2.83 | 1.23 |
| 33.68 | 2.66 | 1.66 |

Example 3

Process for Preparing Crystalline Form α of Compound of Formula (I):

106.3 mg of compound of Formula (I) was dissolved in 10.0 mL tetrahydrofuran to obtain a clear solution. The clear solution was slowly evaporated at 25° C. until solid precipitated. The obtained solid was crystalline Form α.

The XRPD data of the solid prepared in present example is displayed in Table 3.

TABLE 3

| 2theta | d spacing | intensity % |
| --- | --- | --- |
| 5.49 | 16.10 | 4.61 |
| 9.50 | 9.31 | 7.60 |
| 11.06 | 8.00 | 100.00 |
| 14.01 | 6.32 | 5.77 |
| 15.53 | 5.70 | 13.83 |
| 17.25 | 5.14 | 15.88 |
| 18.05 | 4.91 | 41.31 |
| 19.20 | 4.62 | 4.60 |
| 20.64 | 4.30 | 4.37 |
| 22.25 | 4.00 | 27.97 |
| 28.78 | 3.10 | 4.91 |
| 31.55 | 2.84 | 0.92 |
| 33.60 | 2.67 | 1.42 |

Example 4

Figure 7:
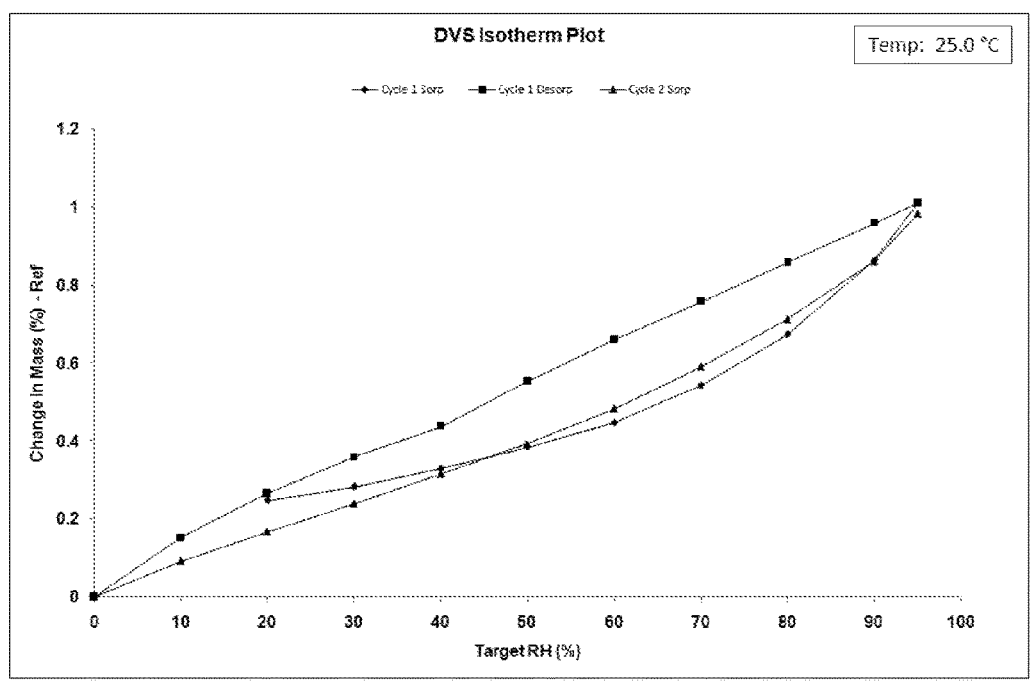
FIG. 7 shows the DVS plot of Form α.

Hygroscopicity Assessment of Form α of Compound of Formula (I):

Hygroscopicity of 10 mg Form α of the present invention was tested using dynamic vapor sorption (DVS). The result is listed in Table 4. The DVS isotherm plot is displayed in FIG. 7.

TABLE 4

| Solid Form | Weight gain under 80% RH |
| --- | --- |
| Crystalline Form α of compound of Formula (I) | 0.67% |

About hygroscopicity characterization description and definition of hygroscopicity (Chinese Pharmacopoeia 2010 edition appendix XIXJ Drug hygroscopic test guidelines, test at 25° C.±1, 80% Relative Humidity)

deliquescent: sufficient water is absorbed to form a liquid;
very hygroscopic: increase in mass is equal to or greater than 15 percent;
hygroscopic: increase in mass is less than 15 percent and equal to or greater than 2 percent;
slightly hygroscopic: increase in mass is less than 2 percent and equal to or greater than 0.2 percent;
no or almost no hygroscopic: increase in mass is less than 0.2%.

The result indicates that crystalline Form α of the present disclosure has a 0.67% weight gain at 80% RH. The hygroscopicity of crystalline Form α of the present disclosure is slightly hygroscopic according to hygroscopic test guidelines.

Example 5

Stability Assessment of Form α Prepared by Example 1 and Anhydrous Form A in CN103648499A:

Form α of the present disclosure and anhydrous Form A in CN103648499A were mixed with a mass ratio of 1:1 and stirred in tetrahydrofuran at 5° C., 25° C. and 50° C. at a rate of 500 r/min for 24 h. The mixed solution was centrifuged to obtain the solid for XRPD test, the testing result was shown in table 5.

TABLE 5

| Temperature | Solvent | Initial form | Stirring time | Final form |
| --- | --- | --- | --- | --- |
| 5° C. | tetrahydrofuran | Form α and anhydrous Form A in CN103648499A | 24 h | Form α |
| 25° C. | tetrahydrofuran | Form α and anhydrous Form A in CN103648499A | 24 h | Form α |
| 50° C. | tetrahydrofuran | Form α and anhydrous Form A in CN103648499A | 24 h | Form α |

The result indicates that anhydrous Form A disclosed in CN103648499A was converted to Form α of the present disclosure at 5° C., 25° C. and 50° C. Thus, Form α of the present disclosure is more stable than anhydrous Form A in CN103648499A.

What is claimed is:
1. A crystalline Form α of compound of Formula (I), the structure of the compound of formula (I) being:

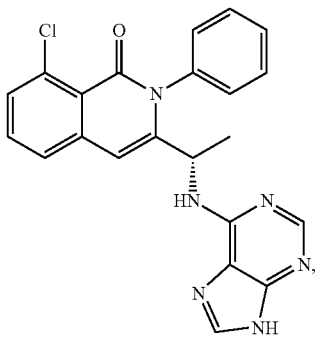

(I)

wherein the X-ray powder diffraction pattern of Form α has characteristic peaks at 2theta values of 5.5±0.2°, 11.1°±0.2°, 15.5±0.2°, 17.2±0.2°, 18.1±0.2°, 22.3±0.2°, and 28.8±0.2°.

2. The Form α according to claim 1, wherein the X-ray powder diffraction pattern is as shown in FIG. 1.

3. A process for preparing Form α of the compound of Formula (I) according to claim 1, wherein the process comprises: adding the solid of the compound of Formula (I) into a crystallization solvent to obtain a suspension, stirring the suspension at 40° C.-60° C., filtering the suspension to obtain a clear solution, cooling the clear solution to −20° C.-10° C., and then obtaining the crystalline Form α.

4. The process according to claim 3, wherein said crystallization solvent is selected from one or more solvents comprising: alcohols, ketones, esters, aromatic hydrocarbons, halogenated hydrocarbons, nitriles, nitroparaffins, cyclic ethers and fatty hydrocarbons.

5. The process according to claim 4, wherein said crystallization solvent is tetrahydrofuran.

6. A process for preparing Form α of the compound of Formula (I) according to claim 1, wherein the process comprises: dissolving the solid of the compound of Formula (I) into a crystallization solvent to obtain a clear solution, and evaporating the clear solution at 10° C.-30° C. until a solid is precipitated, the solid being the crystalline Form α.

7. The process according to claim 6, wherein said crystallization solvent is selected from one or more solvents comprising: alcohols, ketones, esters, aromatic hydrocarbons, halogenated hydrocarbons, nitriles, nitroparaffins, cyclic ethers and fatty hydrocarbons.

8. The process according to claim 7, wherein said crystallization solvent is tetrahydrofuran.

9. A pharmaceutical composition, wherein said pharmaceutical composition comprises Form α according to claim 1 and pharmaceutically acceptable excipients.

10. A method of treating cancer in a subject thereof, comprising administering the Form α according to claim 1 to the subject.

11. A method of treating chronic lymphocytic leukemia and indolent non-Hodgkin's lymphoma in a subject thereof, comprising administering the Form α according to claim 1 to the subject.

* * * * *